(12) United States Patent
Gilboe

(10) Patent No.: US 7,034,553 B2
(45) Date of Patent: Apr. 25, 2006

(54) DIRECT RESISTANCE MEASUREMENT CORROSION PROBE

(75) Inventor: Derek Gilboe, Edmonton (CA)

(73) Assignee: Prodont, Inc., Edmonton (CA)

( * ) Notice: Subject to any disclaimer, the term of this patent is extended or adjusted under 35 U.S.C. 154(b) by 0 days.

(21) Appl. No.: 10/707,329

(22) Filed: Dec. 5, 2003

(65) Prior Publication Data

US 2005/0122121 A1 Jun. 9, 2005

(51) Int. Cl.
*G01R 27/08* (2006.01)

(52) U.S. Cl. .................................. 324/700; 324/691

(58) Field of Classification Search .................. 73/86, 73/152.01; 324/700, 691; 338/28; 340/360
See application file for complete search history.

(56) References Cited

U.S. PATENT DOCUMENTS

| | | | |
|---|---|---|---|
| 3,104,355 A | 4/1955 | Holmes et al | ........... 324/71 |
| 2,735,754 A | 2/1956 | Dravnieks | ........... 23/230 |
| 3,996,124 A | 12/1976 | Eaton et al. | |
| 4,160,948 A | 7/1979 | Tytgat et al. | |
| 4,181,882 A | 1/1980 | Isaacs et al. | |
| 4,326,164 A | 4/1982 | Victor | |
| 4,514,681 A | 4/1985 | Finley et al. | |
| 4,703,254 A | 10/1987 | Strommen | |
| 5,243,297 A | 9/1993 | Perkins et al. | |
| 5,446,369 A | 8/1995 | Byrne et al. | |
| 5,450,765 A * | 9/1995 | Stover | ........... 73/866.5 |
| 5,571,955 A | 11/1996 | Beavers et al. | ........... 73/86 |
| 5,627,749 A * | 5/1997 | Waterman et al. | ........... 702/6 |
| 6,556,027 B1 | 4/2003 | Banks | ........... 324/700 |
| 6,623,616 B1 * | 9/2003 | Malver et al. | ........... 205/775.5 |
| 2002/0153907 A1 | 10/2002 | Yang et al. | |
| 2003/0029232 A1 * | 2/2003 | Felix et al. | ........... 73/86 |

FOREIGN PATENT DOCUMENTS

| | | |
|---|---|---|
| EP | 0 150 552 | 1/1989 |
| GB | 2 150 300 | 6/1985 |
| GB | 2 180 068 A | 3/1987 |
| GB | 2 262 608 | 6/1993 |
| GB | 2 338 307 | 12/1999 |
| GB | 2 352 520 | 1/2001 |
| WO | WO 94/12662 | 6/1994 |
| WO | WO 00/54027 | 9/2000 |
| WO | WO 00/63674 | 10/2000 |

\* cited by examiner

*Primary Examiner*—Walter Benson
(74) *Attorney, Agent, or Firm*—Bennett Jones LLP

(57) ABSTRACT

A direct resistance measurement probe for measuring corrosion levels and material loss. The probe includes a hollow body having a resistive element at one end that is exposed to the environment. The probe can have an internal or external power source that is electrically connected to the resistive element. A meter measures the electrical resistance of the resistive element providing data from which corrosion rates may be ascertained. A temperature sensing device measures the temperature of the resistive element. A pressure sensing device measures the pressure of the environment that the resistive element is subjected to. The probe does not use a comparative or ratiometric reference element.

7 Claims, 5 Drawing Sheets

RESISTANCE PROBE RESPONSE

500
DIRECT RESISTANCE MEASUREMENT CORROSION PROBE

BACKGROUND OF INVENTION

The present invention relates to an apparatus for measuring metal loss in industrial process and downhole environments. In particular, the present invention relates to a probe which permits direct measurement of electrical resistance which can provide an estimation of the metal loss at the surface of industrial or process equipment.

In industrial and process environments the corrosion of pipes and vessels poses a major concern. System failure due to corrosion can result in extensive downtime, can result in widespread systemic damage or failure, and can endanger the health and safety of individuals operating the system. Therefore it is beneficial to accurately monitor corrosion and degradation rates to facilitate the replacement or repair of weakened pipes or vessels before structural failure is experienced.

Probes that assess corrosion levels by measuring electrical resistance are well known. Commonly, the probe is comprised of a metal element that is subjected to the corrosive environment inside the pipe or vessel. The element is made from the same material as the pipe or vessel and because it is being subjected to the same environment as the pipe or vessel, corrosion levels on the metal element can be correlated to corrosion levels on the pipe or vessel. The level of corrosion on the metal element is monitored by assessing its electrical resistance and comparing it to the resistance of a reference element, insulated from the corrosive environment. The measurements involve a ratio-metric comparison of the resistivity of the reference element and the exposed element. The metal elements may project into the pipe or vessel, or alternatively they can be inserted such that they are flush with the pipe of vessel wall thereby facilitating the contemporaneous use of cleaning and monitoring equipment pigs.

There are a number of problems associated with the existing probes. The use of ratiometric measurement to compare a corroding element with a reference element is limited in accuracy and resolution. Current probes do not integrate electronics and memory and rely on transmitting readings to an external analysis and storage system by means of cables or wires. The remote nature of the electronics and memory components results in undesired effects that reduce the precision of the readings obtained from the exposed metal element. The remote electronics and memory components increase the complexity and cost of the corrosion detection system and can often be impractical to utilize in the industrial or field setting. Further, with existing probes, integral temperature compensation must be conducted which increases the complexity of accurate data interpretation. This problem is amplified by the introduction of additional thermal effects due to the manufacturing processes utilized. Also the data obtained from current probes is often difficult to read and interpret or reproduce.

Therefore, there is a need in the art for a direct resistance measurement corrosion probe that overcomes the existing limitations of the prior art.

SUMMARY OF INVENTION

The present invention relates to a probe apparatus for measuring the resistance change of a resistive element comprised of a material similar to the equipment subject to metal loss. The present invention integrates sensory electronics and data storage into the probe such that resistance readings are periodically conducted and are either stored in the probe until they are downloaded by the user for offline interpretation and analysis, or alternatively, they are downloaded as real time measurements. Probes of the present invention also include temperature sensors and optional pressure sensors, so that contemporaneous temperature and pressure readings are obtained.

Accordingly, in one aspect of the invention, the invention comprises a probe for measuring the electrical resistance of a resistive element, for estimating loss of a metal exposed to an environment, comprising:

(a) a sealed hollow body having a first and second end;

(b) a resistive element contained at the first end of the body wherein a surface of the resistive element is exposed to the environment and the resistive element has a similar or identical composition to the exposed metal;

(c) an internal or external power source electrically connected to the resistive element;

(d) a meter for measuring the electrical resistance of the resistive element;

(e) a temperature sensing device for measuring the temperature of the resistive element disposed proximally to the resistive element;

(f) a memory for storing resistance and temperature data; and (g) control means for applying an electric current and potential across the resistive element, receiving the output data of the resistance meter, receiving the output data of the temperature sensing device, and storing said data into the memory wherein the resistance data is associated with the temperature data;

wherein said probe does not use a comparative reference element.

In one embodiment the resistive element is comprised of an electrically conductive metallic element having known dimensions which is compositionally similar or identical to the metal. In one embodiment the probe further comprises a pressure sensor exposed to the environment for measuring the pressure of the particular environment.

In an embodiment, the control means comprises a microchip or a compact electrical circuit comprising a resistance measurement circuit, a temperature measurement circuit, a pressure measurement circuit, which is operatively connected to, or comprises, the memory. In a further embodiment the hollow body comprises, an element carrier at its first end for holding the conductive metal element in the particular environment, a probe body releasably attached to the element carrier and a carrier plug for insertion into the structure that is being exposed to the particular environment at its second end. In another embodiment, the probe body is permanently affixed to the element carrier.

BRIEF DESCRIPTION OF DRAWINGS

The invention will now be described by means of an exemplary embodiment as shown in the accompanying, simplified, diagrammatic not to scale drawings. In the drawings.

DETAILED DESCRIPTION

Figure 1:
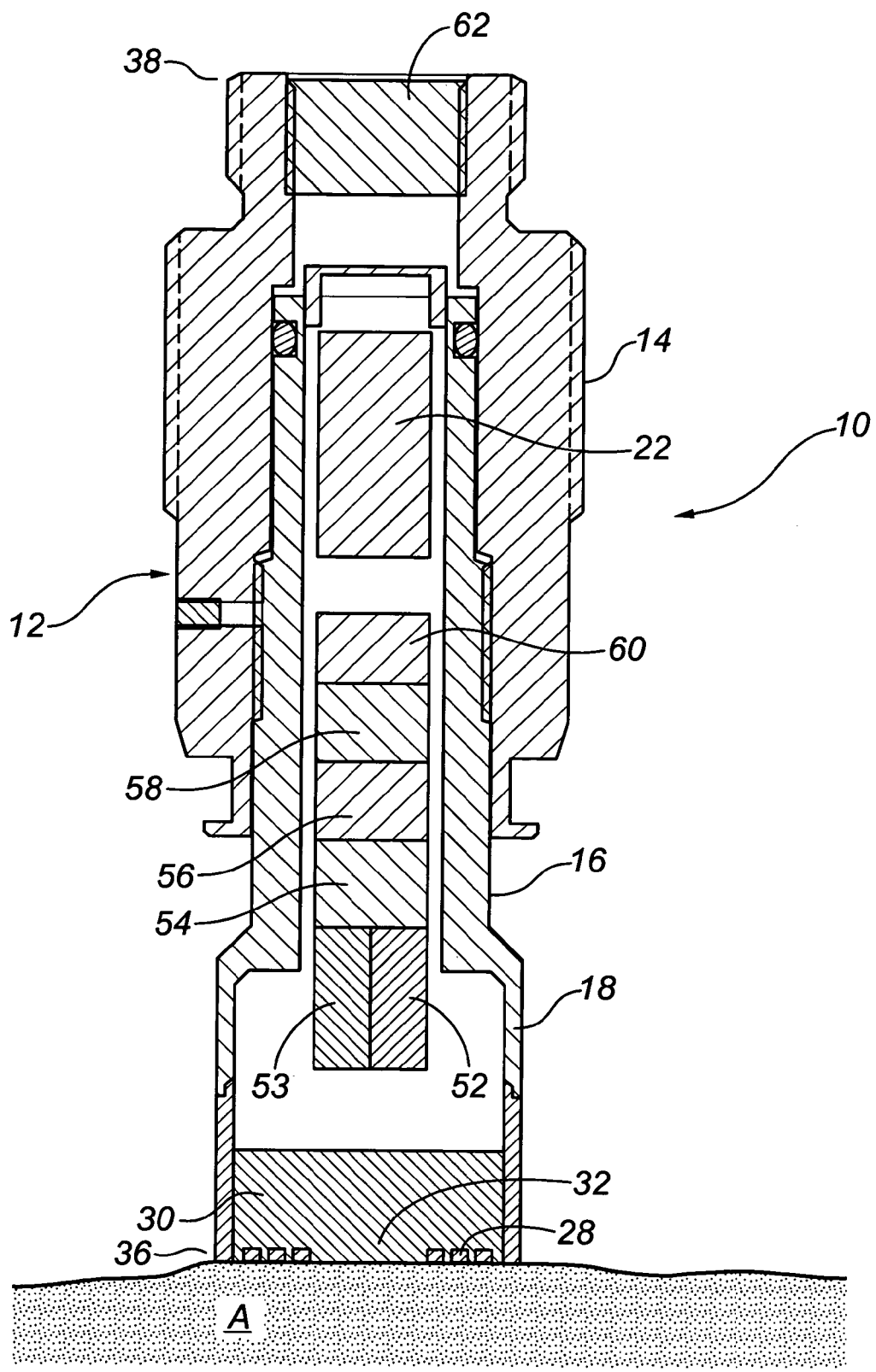
FIG. 1 is a diagrammatic depiction of one embodiment of the present invention.

The present invention relates to a probe for monitoring corrosion in a pipe or vessel. The probe directly measures electrical resistivity of an element, which may be correlated to metal loss of the element. For the purposes of the patent application the following words shall the following meanings: The "environment" means either an erosive or corrosive environment that may be causing metal loss of its containing surfaces. In one example, the environment may be the internal cavity of a pipe through which a process fluid or gas travels or a vessel containing fluid or gas. The metal loss may be occurring on the interior pipe walls. In another example, the environment may be the borehole of an oil and gas well; the metal loss may be occurring on the inner surfaces of the well tubing.

The probe (10) may be used in any environment where metal loss is a concern, including oil and gas wells, production and transmission facilities or industrial process settings. Before describing the probe (10) it is pertinent to describe the theoretical basis underlying its use to measure metal loss in an erosive or corrosive environment.

Metallic materials have predictable electrical properties. These properties have a direct relationship with physical dimensions. Application of basic electrical theory allows the electrical resistance of a metallic sample to be estimated as follows:

$$R = \rho \frac{L}{A} \quad [1]$$

Equation [1] above determines the electrical resistance (R) as a function of the electrical conductivity ($\rho$) multiplied by the ratio of the length (L) and average cross sectional area (A). Resistance values typically are in the order of 10–100 milliohms (m$\Omega$). Therefore, through the measurement of electrical resistance, one or more of the physical dimensions of a metallic object can be determined.

Corrosion can be determined by using a conducting element of known dimensions that is exposed on one surface to the corrosive environment. When the element is rectangular in shape, the metal loss on the single surface can be described using the following equation:

$$A = wt = \rho \frac{L}{R} \Rightarrow t = \rho \frac{L}{Rw} \quad [2]$$

Equation [2] shows the determination of the thickness (t) from the resistance (R), which holds true when the length (L) and width (w) of the metallic element remain constant. The logarithmic response of this relationship is non-linear but predictable. Knowing the electrical properties of the element allows the independent variables, length (L) and width (w) to be combined with the electrical conductivity ($\rho$) and restated as a constant (k) for the sensing device, resulting in equation [3]:

$$t = \frac{k}{R}$$

Direct measurement of the resistance (R) allows the metallic element to be used for a life span approaching the complete thickness of the element.

An additional issue relating to the measurement of metal loss is the effect of temperature. All metals experience thermal expansion. This will result in additional changes in the resistivity in a linear fashion as shown in equation [4] below where the length (L) changes by a material specific constant ($\alpha$) multiplied by the change in temperature ($\Delta T$). This effect alters all three physical properties dimensions and can be compensated for through theoretical calculations, but it is only relevant between two readings where a temperature differential occurs. When the temperature is constant between readings, the thermal effect is nil.

$$L = L_o + \alpha L_o (\Delta T) = L_o (1 + \alpha \Delta T) \quad [4]$$

The present invention may now be described having reference to the accompanying Figures. As shown in FIG. 1, the probe (10) has a sealed hollow body (12) formed by two pieces (12A, 12B). The first piece (12A) defines the first end (36) of the probe while the second piece (12B) defines the second end (38). Alternatively, the sealed hollow body may comprise a single piece with the second end (38) being configured for attachment means such as a plug or flange. The use of a single piece or two pieces for the hollow body permits the use of alternate methods to insert the first end of the probe (36) into the environment. As depicted in FIG. 1, the probe (10) is placed into the apparatus that is being monitored such that that first end (36) is immersed in the environment (A). The hollow body (12) is sealed at both ends (36, 38) thereby protecting the contents of the hollow body from the environment. Furthermore, an O-ring seal is provided between the first and second pieces of the probe body (12).

Figure 2A:
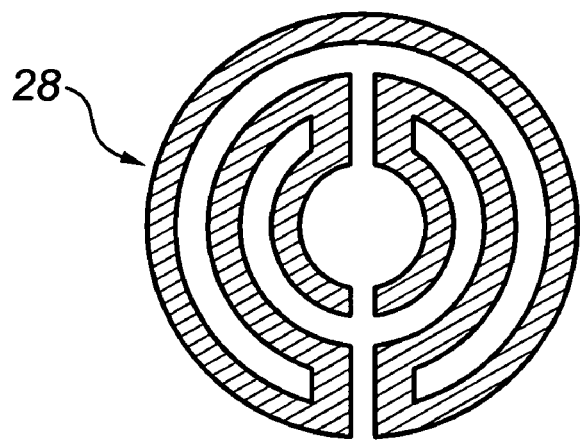
FIG. 2A is a plan view of the resistive element of one embodiment of the present invention.
Figure 2B:
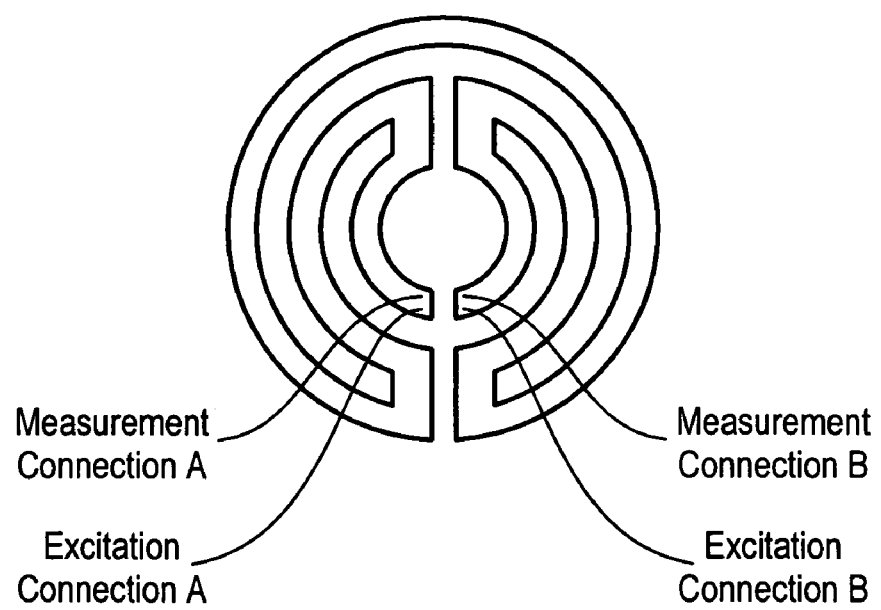
FIG. 2B is a similar view showing the electrical contact points and resistance measurement points of the resistive element.
Figure 3:
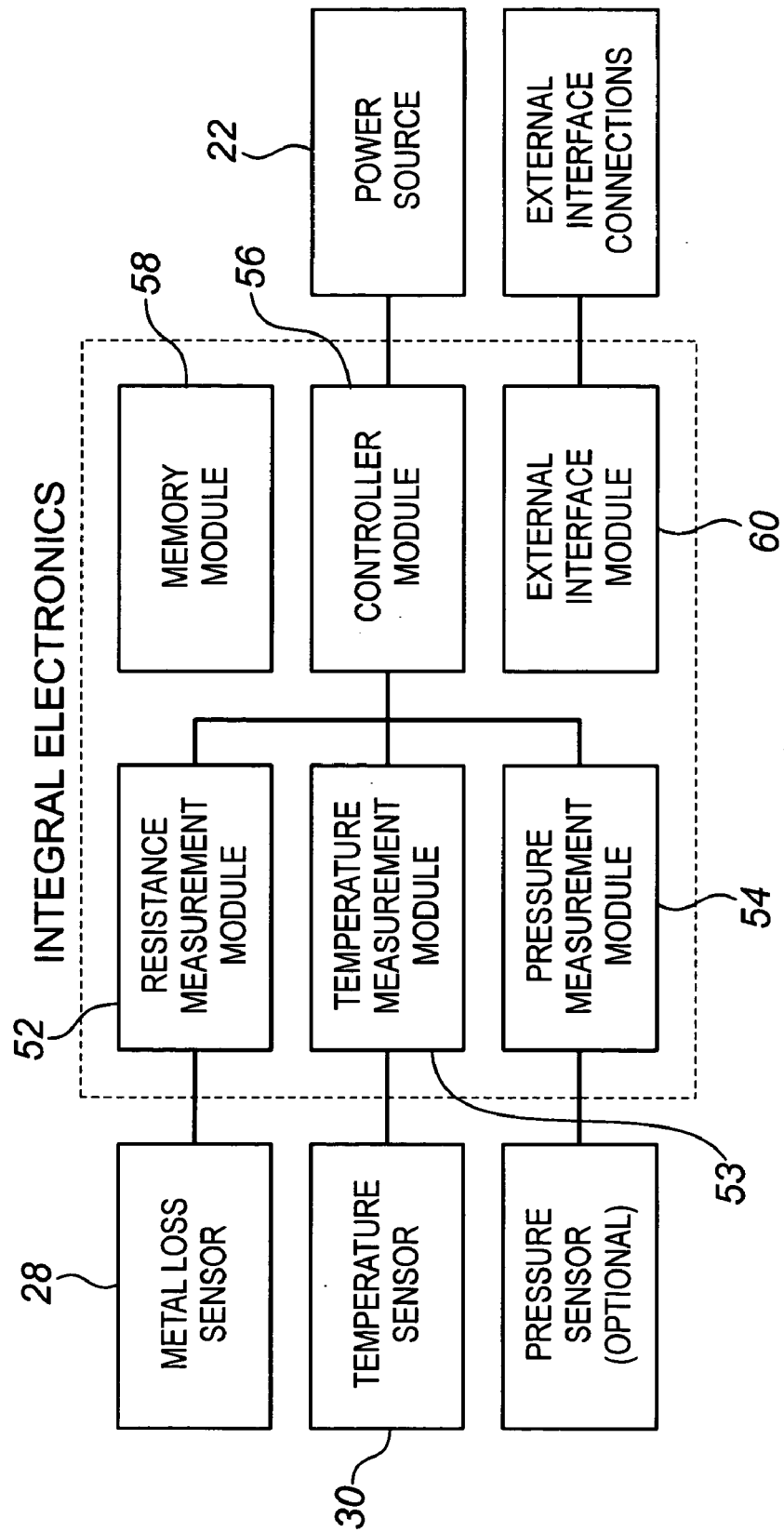
FIG. 3 is a schematic block diagram of one embodiment of the probe circuitry.

The probe (10) has a resistive element (28) located at its first end (36) having one surface of the resistive element (28) being directly exposed to the environment (A). As shown in FIG. 2, the resistive element (28) is comprised of an electrically conductive metallic element of known dimensions (hereinafter the "CME"). In one embodiment, the CME (28) may be a planar strip of metal having a relatively constant width configured to maximize its length within the confines of the probe. One embodiment of the CME is illustrated in FIG. 3. The planar strip follows a symmetrical path inscribed with a circle. The two ends of the CME strip are conveniently adjacent each other near the center of the CME. The form and shape of the CME (28) may be varied depending on the shape and configuration of the probe. The necessary attributes of the CME are that it be formed of a metal strip having a consistent cross-section, the strip having a length to width ratio of at least 10:1 and preferably about 20:1, and a thickness of at least 0.50 mm. The CME example shown in FIG. 2 may have an outside diameter of about 1.75" (44.5 mm). The total path or length of the CME shown is about 11.3" (287 mm), with a width of about ⅛" (3.2 mm). The thickness of a CME may vary between about 0.025" (0.64 mm) to about 0.063" (1.59 mm).

The CME (28) may be constructed from a similar or identical metallic material as the instrument that is being monitored, thereby allowing the user to equate metal loss on the CME (28) with metal loss on the instrument. The resistivity of the CME (28) may be measured by electrically exciting the CME (28) with an alternative current square wave signal of a fixed current typically at a frequency between 100 and 300 Hz. In one embodiment, the CME (28) has a starting thickness of 1.27 mm to 1.59 mm (depending on the element configuration) with a minimum detectable resistance change of approximately 3 μΩ, corresponding to a metal loss of approximately 50 pm. This sensitivity provides a significant advantage for the detection of metal loss and permits accurate reading of the CME (28) to degradation levels of up to 90%, thereby providing a high long life expectancy of the probe of up to double existing probes.

The connections to the CME (28) may comprise two conductive paths (not shown) constructed from the same material as the CME (28) that attach to an unexposed surface of the CME (28). The conductive paths may be attached to the CME (28) by any suitable attachment means however, an autogenously welded joint promotes optimal electrical properties. The use of the same material as the CME (28) in the conductive paths, and the use of an autogenous joint eliminates or greatly reduces thermocouple and temperature effects which can impair the accuracy of the probe (10) readings.

Figure 4:
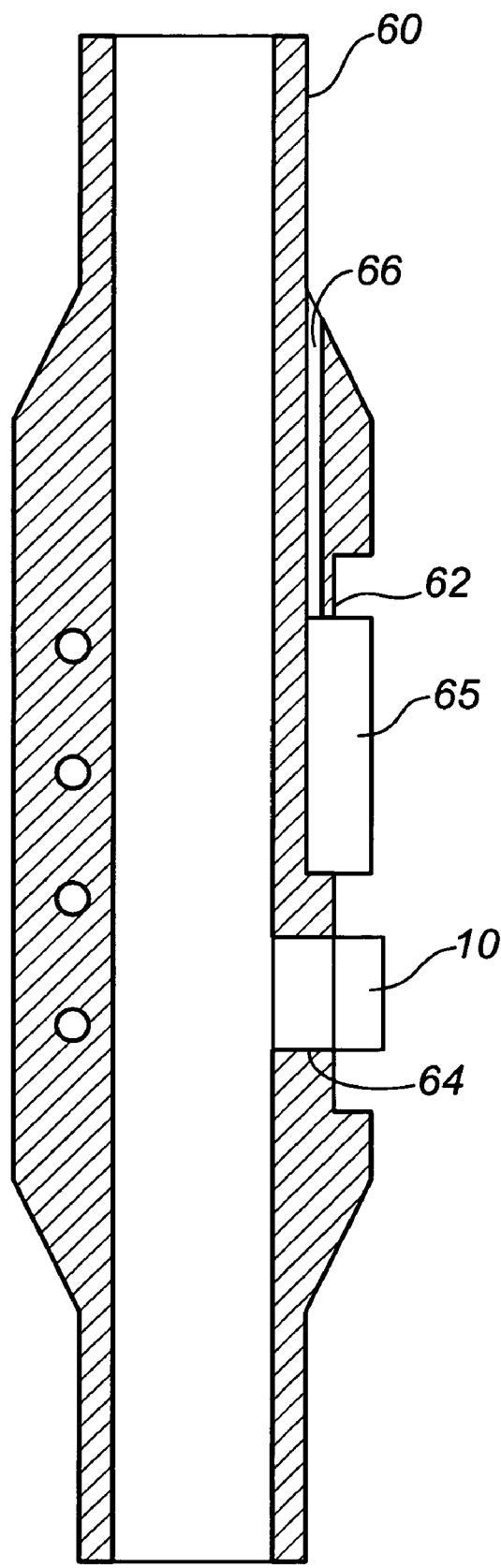
FIG. 4 is cross sectional side view of one embodiment of a down hole monitoring assembly.
Figure 5:
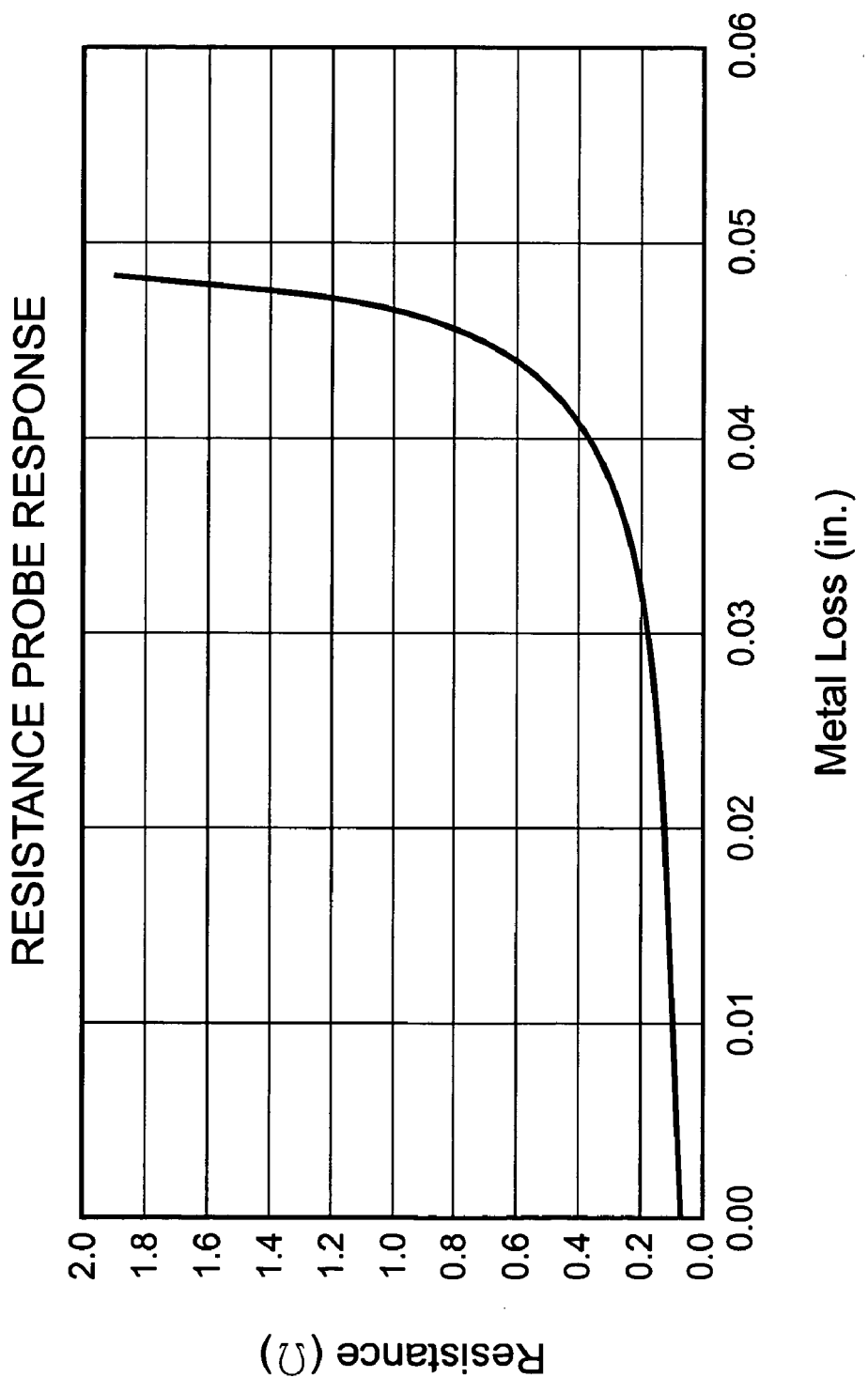
FIG. 5 is a graph illustrating the relationship of resistance to metal loss for the resistive element.

The probe (10) has an electrical power source that may be an internal battery (22) as shown in FIG. 1, or an external power supply. If an internal power source is used, the power source must be sufficiently small enough to be contained within the probe (10). A suitable internal power source may be a lithium-ion battery, however other suitable internal electrical power sources known in the art may also be utilized. The internal power source may be rechargeable or replaceable. In one embodiment the probe (10) may be powered by an external power source connected to a power connection (62) on the probe (10) as depicted in FIG. 4. Power from the external power source may be conducted to the probe (10) by means of an ordinary wire. Although power sources of varying magnitudes may be used, voltages will typically be less than six volts with currents of three amperes, or less.

As shown schematically in FIG. 4, the probe (10) has a resistance measurement module (52) for measuring the electrical resistance of the resistive element (20). In one embodiment the resistance measurement module (52) comprises a circuit containing a meter for measuring the resistivity of the resistive element, and a switch means for governing the flow of electrical energy to the resistive element (28).

The probe (10) also has a temperature sensing device (30). The temperature sensing device (30) may be a thermocouple, and is preferably disposed immediately adjacent to the unexposed surface of the CME (28). The temperature sensor (30) provides a temperature reading of the CME (28) at the rime that its resistivity is measured. The temperature reading is required if compensation for thermal expansion (or lack thereof) of the CME (28) is to be calculated as discussed above. The probe may also have a pressure sensor (32) that is exposed to the environment in a position proximate to the CME (28). The pressure sensor (32) provides a pressure reading of the environment at the time that the resistivity is of the CME (28) is measured. The pressure level of the environment is a variable that can be accounted for in the metal loss calculations. As shown in FIG. 3, the probe (10) has a temperature measurement module (53) and a pressure measurement module (54) connected to the temperature sensing device (30) and the pressure sensor (32). This module is capable of simultaneously reading the temperature of the CME (28) from the temperature sensing device (30) and of reading the pressure of the environment from the pressure sensor (32) at the time that the resistivity of the CME (28) is being measured.

The probe has a memory module (58) for storing resistance, temperature and pressure data. The memory may comprise solid state memory chips as are well known in the art, connected to the measurement modules (52, 53, 54) for recording and storing the resistivity, temperature and pressure readings until such time as this information is offloaded from the probe (10). The memory module (58) may also be configured such that the stored information for each reading also includes information regarding the probe type, the CME type and a time stamp. The probe (10) also has means for downloading information from the memory module (58) to an external data storage and analysis system. As shown in FIG. 4, the means for downloading information may be comprised of an external interface module (62). In one embodiment, the interface module (62) may be a hard wire connection, which facilitates real time monitoring. In another embodiment, the interface (62) may be configured for the use of a wireless connection system facilitating the transmission of information to a handheld device if desired. The configuration of the download means will be largely governed by the location of the probe, and by the type of instrument that is being monitored.

The probe (10) has a control means for controlling the measurement modules and the memory. The control means may comprise a controller module (56) as shown in FIG. 4. The controller module (56) manages all of the data collection, data transmission and power transmission using internal circuitry switching. The controller module (56) activates the measurement circuits at preset time intervals or upon command.

It should be understood that for ease of explanation the various modules have been described as separate units, however the resistance measurement module (52), the temperature measurement module (53) and pressure measurement module (54), the controller module (56), the memory module (58) and the external interface module (60) may comprise circuits contained on a single microchip that is connected to the power source (22), to the sensing devices and to the resistive element (28). The electronics in the probe (10) may be located immediately adjacent to the CME (28) further reducing and eliminating any detrimental thermocouple effects.

In use, a baseline resistance measurement and temperature measurement is taken immediately upon installation of the probe. This reading will be stored in memory and used as a reference point to compare subsequent readings to. The resistance measurements may be converted to a measurement of the thickness of the CME (28), using the formulae detailed above. Temperature adjustments are only necessary if the measurement temperature is different from the baseline temperature used to establish a baseline resistance reading. In FIG. 6, the electrical resistance of a CME which was initially 0.05" (1.27 mm) is shown. The increase in resistance is relatively linear until approximately 40% of the thickness of the CME is lost, at which point the resistance begins to increase exponentially. However, the amount of metal loss may be assumed to be linear between any two consecutive measurements. This assumption is based on the trapezoidal rule of mathematics which permits the approximation of any curve by a series of trapezoids.

Pressure adjustments are only required when the operating pressure levels equal or exceed the levels required to physically deform the CME. When the pressure of the environment reaches levels such that the CME will physically deform, by either plastic or elastic means, adjustments for pressure are necessary and are undertaken using conventional and accepted practices.

As depicted in FIG. 1, in one embodiment of the probe (10), the first end of the hollow body (36) may be comprised of an element carrier (18) for securely positioning the CME (28) such that one surface is exposed to the environment. The element carrier (18) releasably attaches to one end of a central probe body (16). The attachment means may be an adjustment nut, or such other suitable attachment means as are commonly used in the art. The other end of the central probe body (16) attaches to a carrier plug (14) that extends to the second end of the probe (38). The carrier plug (14) facilitates the sealed insertion of the probe (10) into the pipe, tubing or vessel that is being monitored, thereby preventing the escape of corrosive or erosive substances from the environment. The hollow body (12) may be constructed from any suitable corrosion resistant material. The contents of the hollow body (12) may be embedded in an insulating solid such as silicon, or such other suitable insulating material. This embodiment is well suited for the monitoring of surface apparatus.

As shown in FIG. 4, in another embodiment, a monitoring assembly may be designed to facilitate the use of the probe (10) in the downhole environment in oil and gas wells. The down hole assembly is comprised of a hollow carrier (60) that is sized to provide the same flow cross section as the production tubing while the outside diameter is sized to ensure clearance for the well casing. Both ends of the hollow carrier (60) may be threaded to facilitate insertion into the production tubing. The probe (10) is securely inserted into an opening (64) in the carrier walls such that one surface of the resistive element is exposed to the interior of the hollow carrier (60). The hollow carrier (60) has an electronics receptacle (59) adjacent to the opening (60). An external connector (65) is mounted in the electronics receptacle (62) and is connected to the probe (10). The probe electronics in the probe (10) and the connections to the external connector may be encased in an epoxy and secured to the hollow carrier (60) with a carrier lock having a spring pin locking mechanism (not shown). The probe electronics may be connected to the surface of the well by means of a wire or cable that runs from the external connector (65) through a wire channel hollow carrier (66) and up the exterior surface of the production tubing to the surface.

As will be apparent to those skilled in the art, various modifications, adaptations and variations of the foregoing specific disclosure can be made without departing from the scope of the invention claimed herein. The various features and elements of the described invention may be combined in a manner different from the combinations described or claimed herein, without departing from the scope of the invention.

The invention claimed is:

1. A probe for measuring the electrical resistance of a resistive element, for estimating loss of a metal exposed to an environment, comprising:
   (a) a sealed hollow body having a first and second end;
   (b) a resistive element contained at the first end of the body wherein a surface of the resistive element is exposed to the environment and the resistive element has a similar or identical composition to the exposed metal;
   (c) an internal or external power source electrically connected to the resistive element;
   (d) a meter for measuring the electrical resistance of the resistive element;
   (e) a temperature sensing device for measuring the temperature of the resistive element disposed proximally to the resistive element;
   (f) a memory for storing resistance and temperature data;
   (g) control means for applying an electric current and potential across the resistive element, receiving the output data of the resistance meter, receiving the output data of the temperature sensing device, and storing said data into the memory wherein the resistance data is associated with the temperature data;
   (h) an element carrier at its first end for holding the resistive element in the particular environment;
   (i) a probe body releasably attached to the element carrier; and
   (j) a carrier plug for insertion into the structure that is being expose to the particular environment at its second end, the carrier plug being fixed to the probe body,
   wherein said probe does not use a comparative reference element.

2. The probe of claim 1 wherein the resistive element is comprised of an electrically conductive metallic element having known dimensions which is compositionally similar or identical to the metal.

3. The probe of claim 1 wherein the temperature measuring device is disposed proximally to the resistive element.

4. The probe of claim 1 further comprising a pressure sensor exposed to the environment for measuring the pressure of the particular environment.

5. The probe of claim 1 wherein the control means comprises a compact electrical circuit comprising a resistance measurement circuit, a temperature measurement circuit, a pressure measurement circuit, which is operatively connected to, or comprises, the memory.

6. The probe of claim 5 wherein the compact electrical circuit comprises a microchip.

7. The probe of claim 1 wherein the probe body is permanently affixed to the element carrier.

* * * * *